United States Patent [19]
Keilbach

[11] Patent Number: 5,929,981
[45] Date of Patent: Jul. 27, 1999

[54] SYSTEM FOR MONITORING CONTAMINATION OF OPTICAL ELEMENTS IN A RAMAN GAS ANALYZER

[75] Inventor: Kevin A. Keilbach, Boulder, Colo.

[73] Assignee: Ohmeda Inc., Louisville, Colo.

[21] Appl. No.: 08/665,387

[22] Filed: Jun. 18, 1996

[51] Int. Cl.⁶ .................................................. G01N 21/00
[52] U.S. Cl. ............................ 356/73; 356/446; 356/437
[58] Field of Search ..................................... 356/445–448, 356/335–339, 73, 300, 432–444, 340–343, 246, 318, 301, 319, 418, 237.1–237.6; 372/107–109, 75, 69; 250/574, 573, 575–577, 338.5, 339.01–339.09

[56] References Cited

U.S. PATENT DOCUMENTS

| | | |
|---|---|---|
| Re. 34,153 | 12/1992 | Benner et al. . |
| 3,436,152 | 4/1969 | Compton et al. . |
| 3,526,461 | 9/1970 | Lindahl et al. . |
| 3,614,462 | 10/1971 | Lean et al. . |
| 3,947,131 | 3/1976 | Karl ........................................ 356/445 |
| 4,286,876 | 9/1981 | Hogg et al. . |
| 4,555,634 | 11/1985 | Muggli et al. . |
| 4,676,639 | 6/1987 | Van Wagenen . |
| 4,767,213 | 8/1988 | Hummel . |
| 4,784,486 | 11/1988 | Van Wagenen et al. . |
| 4,808,813 | 2/1989 | Champetier . |
| 4,885,473 | 12/1989 | Shofner et al. . |
| 4,902,131 | 2/1990 | Yamazaki et al. . |
| 4,965,454 | 10/1990 | Yamauchi et al. . |
| 5,135,304 | 8/1992 | Miles et al. . |
| 5,153,671 | 10/1992 | Miles . |
| 5,245,405 | 9/1993 | Mitchell et al. . |
| 5,255,089 | 10/1993 | Dybas et al. . |
| 5,256,886 | 10/1993 | Wolf et al. . |
| 5,313,072 | 5/1994 | Vachss . |
| 5,341,206 | 8/1994 | Pittaro et al. . |
| 5,408,314 | 4/1995 | Perry et al. . |
| 5,432,610 | 7/1995 | King et al. . |
| 5,452,084 | 9/1995 | Mitchell et al. . |

FOREIGN PATENT DOCUMENTS

| | | |
|---|---|---|
| 0 493 815 | 12/1991 | European Pat. Off. . |
| 0 557 658 | 9/1993 | European Pat. Off. . |

OTHER PUBLICATIONS

Sanders "High Precision . . . Mirrors"; Applied Optics Jan. 1997 vol. 16 No. 1.

*Primary Examiner*—K P Hantis
*Attorney, Agent, or Firm*—Holme Roberts & Owen LLP

[57] ABSTRACT

A photodetector is used to monitor contamination of optical elements within an optical system. The photodetector is aligned to detect nonspecular/diffuse reflections attributable to surface irregularities of particulate matter residing on the surfaces of the optical elements within the system. An increase in the intensity of the nonspecular reflections corresponds to increased levels of contamination on the surface of the optical element. An electronic detector circuit performs signal processing on the photodetector output signal and generates an output signal corresponding to the contamination level. In another aspect of the invention, the photodetector circuit is incorporated into a Raman gas analysis system. The invention also provides a method for detecting nonspecular reflection in an optical resonant system by generating and resonating an optical energy beam in an optical resonant cavity so as to irradiate an optical element within the cavity; detecting optical energy reflecting off the optical element; and generating an output signal functionally related to the intensity of the detected optical energy.

13 Claims, 6 Drawing Sheets

SYSTEM FOR MONITORING CONTAMINATION OF OPTICAL ELEMENTS IN A RAMAN GAS ANALYZER

FIELD OF THE INVENTION

The invention relates to a method and apparatus for detecting nonspecular reflections from optical elements in a Raman gas analyzer system to monitor the degree of contamination in the system.

BACKGROUND OF THE INVENTION

Raman light scattering has been successfully used in critical care situations to continuously monitor a patient's respiratory gases. This technique is based on the effect which occurs when monochromatic light interacts with vibrational/rotational modes of gas molecules to produce scattered light which is frequency shifted from that of the incident radiation by an amount corresponding to the vibrational/rotational energies of the scattering gas molecules. If the incident light photon loses energy in the collision, it is re-emitted as scattered light with lower energy and consequently lower frequency than the incident photon. In a similar manner, if the incident photon gains energy in the collision, it is re-emitted as scattered light with higher energy and higher frequency than the incident photon. Since these energy shifts are species-specific, analysis of the various frequency components present in the Raman scattering spectrum of a sample provides chemical identification of the gases present in the scattering volume. The intensity of the various frequency components, i.e., Raman spectral lines, provides quantification of the gases present, providing suitable calibrations have been made. In this manner, Raman light scattering can be employed to determine the identity and quantity of various respiratory and anesthetic gases present in a patient's breath in operating room and intensive care situations.

Systems developed for analysis of gases in critical care situations utilizing Raman scattering typically employ gas cells which contain a sample of the patient's respiratory gas to be analyzed. One such system is described in U.S. Pat. No. 4,784,486, entitled "MULTI-CHANNEL MOLECULAR GAS ANALYSIS BY LASER-ACTIVATED RAMAN LIGHT SCATTERING", issued to Van Wagenen et al. The gas cell is located either within the resonant cavity of a laser or outside the cavity. In an intracavity system, such as that described by Van Wagenen, a laser beam is directed through a resonant cavity such that it intercepts a respiratory gas sample within a gas cell. An end mirror located at one end of the resonant cavity redirects light incident from a plasma discharge tube back through the resonant cavity, where it again passes through the gas cell and back into the plasma discharge tube. A Brewster prism may be mounted near the end mirror to select the desired wavelength and polarization state of the lasing light. The end mirror and Brewster prism are both mounted on one or more plates of an alignment assembly. Raman scattered light from the gas analysis region within the gas cell is collected by collection optics and directed through one or more interference filters or other means of wavelength discrimination. The collection optics and interference filters and possibly focusing optics in turn transmit the Raman scattered light to appropriate detectors for quantifying each specific Raman signal and thus each specific gas comprising the respiratory gas sample.

Intracavity systems possess the advantage that they achieve a much greater Raman scattering intensity than systems in which the Raman scattering occurs outside of the laser resonant cavity. This greater intensity is a result of the fact that a laser beam transiting an intracavity arrangement propagates through the gas sample many times, with a correspondingly higher time-integrated intensity of Raman scattered light being collected from the gas sample. In contrast, an external arrangement of the gas cell may allow the laser beam fewer passes through the gas sample. While intracavity systems benefit from a greater Raman signal strength than do systems having the gas cell located outside the laser resonant cavity, the resonator optics must be positioned with extreme accuracy for this advantage to be realized, since the multiple reflection of the laser beam within the cavity magnifies any misalignment of the cavity end mirror. Similarly, alignment and optimal component performance is critical for external resonant systems. Consequently, the cavity end mirror, the Brewster prism (if present), and the central axis of the laser plasma tube must all be aligned almost perfectly with respect to each other at all times during operation of the gas analysis system. Additionally, transmission of the laser beam through windows, lenses, prisms, etc. and reflection of the laser beam from mirrors, etc. must be maintained at an optimal level or system performance will degrade due to loss of laser power.

In the intracavity gas cell systems discussed above, windows are commonly provided on either end of the gas cell to protect surrounding optical elements and filters from contaminants which may be present in the gas sample. The windows further serve to confine the gas sample within the gas cell, thereby minimizing the volume of the sample and thus improving the detector's response time. In some systems, the gas cell windows are oriented at Brewster's angle to select and improve the transmission of a particular polarization state of light passing through the sample. In this manner, optical losses in the laser beam which passes through the cell are minimized. However, the gas sample, in combination with particulates often carried with the sample, may contaminate the cell windows and degrade the performance of the system. This contamination may result in undesirable light absorption and/or scattering with a consequent decrease in the laser power circulating through the sample cell. If untreated, this contamination will eventually cause the system to cease to function properly.

The problem of window and cavity optics contamination has been partially solved by providing an air dam around the optics of the laser system to shield the optics from contaminated samples. Systems for providing such an air dam are disclosed in U.S. Pat. No. 5,135,304, entitled "GAS ANALYSIS SYSTEM HAVING BUFFER GAS INPUTS TO PROTECT ASSOCIATED OPTICAL ELEMENTS", issued to Miles et al. and U.S. Pat. No. 5,153,671, entitled "GAS ANALYSIS SYSTEM HAVING BUFFER GAS INPUTS TO PROTECT ASSOCIATED OPTICAL ELEMENTS", issued to Miles. In intracavity systems such as those disclosed in U.S. Pat. No. 5,135,304, the sample of gas to be analyzed is injected near the center of the array of detectors. Simultaneously, a buffer gas such as nitrogen or filtered air is injected on the sides of the analyzer cavity. Both gas streams are exhausted at an intermediate point. This system advantageously provides a pure gas sample near the detectors while protecting the optics of the resonant cavity from contamination carried by the sample gas.

In spite of the advances made in protecting the resonant cavity optics from contamination, individual portions of the resonant cavity, including the end mirrors, gas cell windows, lenses, prisms, laser plasma tube, etc. must still occasionally be disassembled and cleaned of contamination, repaired or replaced. At such times, the optical elements are disassembled and repaired or cleaned, then reassembled. The high degree of precision required of the optical alignment of the system, including the alignment of the end mirror, Brewster prism (if present), and plasma discharge tube, renders field repairs difficult. Thus, most repairs are presently made at the factory where the system can be placed on an optical bench or fixture for precision alignment of the components.

A decision to repair resonant cavity optics is typically made based: (1) on the number of hours such optics have been in service; (2) on some periodic service interval; or (3) when a human operator notices degradation in the functional performance of the unit. Decisions to maintain resonant cavity optics on such bases may result in optical performance degradation to the extent that the cavity no longer performs at an optimal level. Moreover, the lack of a quantifiable basis on which to predicate maintenance of the cavity optics also may result in too frequent, and hence, unnecessary maintenance. A more cost effective basis for justifying such maintenance would be based on some quantifiable performance criteria of the cavity. Therefore, a need exists for a method and system for monitoring the level of particulate contamination on the surfaces of the optical elements in the cavity.

As described above, progress has been made in preventing contamination of the optical elements in Raman gas analyzer systems. However, in present systems, the most prevalent means for monitoring the system for contamination is to monitor the total laser power circulating in the cavity. Since this is a relatively large number compared to the losses initially caused by contamination, it does not provide a very sensitive measurement for contamination and it does not provide information which is useful for localizing the source of contamination. Furthermore, other factors affect total laser power circulating in the cavity, including: contamination of any one of the optical surfaces; misalignment of the optical components; occlusion of the intracavity space; increased Raleigh scattering by gas constituents in the measurement cell; or malfunction of the laser gain medium. Heretofore, no systems have incorporated means specifically designed for detecting and measuring contamination at selected locations in the system. Thus, contamination of the laser optics in the laser cavity from dust, dirt, particulate matter or film build up is still a major problem which can make it difficult to sustain reliable lasing in an unsealed laser resonator.

SUMMARY OF THE INVENTION

The present invention includes a contamination monitor which solves many of the problems mentioned above by placing a light sensitive detector in close proximity to an optical element (including mirrors, windows, prisms, lenses, etc.) to be monitored. The detector is positioned at an angular orientation with respect to the optical element such that the detector receives nonspecular light which is reflected or scattered from the optical element. The detector outputs a signal which is a measure of the intensity of the nonspecular light received. The magnitude of the detector output signal provides an indication of the degree of contamination on the optical component. This contamination monitor thus provides information which is more specific than previously available, i.e., if several optical components are being monitored, the output signals from the respective detectors provide quantitative information which indicates the relative degree to which each optical component is contaminated. Armed with this information, trouble shooting and repair is greatly enhanced.

In accordance with a first aspect of the present invention, a system for monitoring contamination of the optical elements within an optical system is disclosed. A photodetector mounted adjacent to an optical element within an optical system is aligned to detect nonspecular reflections attributable to surface irregularities due to contaminates, typically in the form of particles, residing on the surface of the optical element. An increase in the intensity of the nonspecular reflections corresponds to increased levels of contamination. A detector electronics circuit performs signal processing on the photodetector output signal and generates an output signal related to the intensity of the detected reflections.

In accordance with another aspect of the invention, the photodetector circuit is incorporated into a Raman gas analysis system. The photodetector detects nonspecular optical reflections from the optical elements within an optical resonant cavity comprising the system. Such nonspecular reflections result from the accumulation of particulate matter (contaminants) on the surfaces of the optical elements. The particulate matter is conveyed by test gases introduced into a gas analysis cell comprising the system.

The invention also provides a method for determining the degree of contamination in an optical system by detecting the intensity of nonspecular optical reflections off optical elements within the system. The method includes propagating an optical beam by means of optical elements; detecting nonspecular optical reflections from at least one of the optical elements; and generating an output signal functionally related to the intensity of the detected nonspecular optical energy.

An important advantage of the invention is that it may be used to monitor the performance of an optical system. The invention provides a quantitative criteria by which a determination may be made regarding the necessity of cleaning the optical elements within the system. Without such a criteria, maintenance of the system may be performed on some basis not necessarily relevant to the actual performance of the system.

In a first embodiment, the invention is a system for detecting contamination on a surface of an optical element in an optical system comprising: an optical energy source disposed to generate a beam of optical radiation for transmission in the optical system and irradiation of the optical element; an optical energy detector positioned to detect nonspecular optical energy scattered from the surface of the optical element; and a detector circuit operably coupled to the optical energy detector to receive signals from the optical energy detector which are representative of an intensity of the optical energy scattered from the surface of the optical element detected by the optical energy detector, the detector circuit having an output which produces an electronic signal which is representative of the intensity of the optical energy scattered from the surface of the optical element. In this embodiment, the optical energy detector may further comprise one of either a photodiode, a photomultiplier tube or a phototransistor; the optical energy source may further comprise a laser having a resonant cavity wherein the optical element is located within the laser resonant cavity. Additionally, the optical energy detector may be mounted within the laser resonant cavity.

The invention also includes a method for detecting contamination of an optical element in an optical system comprising the steps of: generating an optical beam; positioning the optical element in the optical system; irradiating the optical element with the optical beam; positioning an optical detector with respect to the optical element such that the optical detector receives nonspecular optical radiation scattered from the optical beam by contamination located on a surface of the optical element; detecting the nonspecular optical radiation scattered from the surface of the optical element; and generating an output signal which is representative of an intensity of the nonspecular optical radiation scattered from the surface of the optical element. The step of detecting may further comprise the step of selecting either one of a photodiode; a phototransistor or a photomultiplier tube. Additionally, the step of generating an optical beam may further comprise the step of selecting a laser having a resonant cavity; and the step of positioning an optical detector may further comprise the step of positioning the optical detector within the laser resonant cavity.

A second embodiment includes an apparatus for the analysis of gases in a gas sample by Raman light scattering comprising: a laser light source for producing and transmitting a laser beam of optical radiation along an optical path; a gas sample cell to receive and hold the gas sample in an interior region of the gas sample cell, wherein the gas sample cell is positioned in the optical path to receive the laser beam of optical radiation from the laser light source; a Raman scattered light detector positioned with respect to the gas sample cell such that it receives and detects Raman scattered light from the gas sample; an optical element positioned in the optical path; and a contamination detector positioned with respect to the optical element such that it receives and detects nonspecular light scattered out of the laser beam by the optical element. In this embodiment, the laser light source may further comprise a laser having a resonant cavity and the gas sample cell and the optical element may be located within the laser resonant cavity. Additionally, the optical element may further comprise any one of a window, lens, prism, Brewster window or filter. In some configurations, this embodiment further comprises an electronic circuit operably coupled to the contamination detector and configured to generate an output signal related to the intensity of the nonspecular light scattered out of the laser beam by the optical element. The contamination detector may further comprise any one of a photodiode, a photomultiplier tube or a phototransistor. Additionally, in some embodiments, the gas sample cell may further comprise a passive resonant cavity which is pumped by the laser light source.

A third embodiment of the invention includes an apparatus for the analysis of gases in a gas sample by Raman light scattering comprising: a laser light source for producing and transmitting a laser beam of optical radiation along an optical path, the laser light source including a resonant cavity having losses in the range of from approximately 1000 parts per million (PPM) to 2500 PPM; a gas sample cell positioned within the resonant cavity to receive and hold the gas sample in an interior region of the gas sample cell, wherein the gas sample cell is positioned in the optical path to receive the laser beam of optical radiation from the laser light source; and a Raman scattered light detector positioned with respect to the gas sample cell such that it receives and detects Raman scattered light from the gas sample.

These and other characteristics of the present invention will become apparent through reference to the following detailed description of the preferred embodiments and accompanying drawings.

BRIEF DESCRIPTION OF THE DRAWINGS

Throughout the figures, like reference numbers refer to like elements.

DETAILED DESCRIPTION OF THE PREFERRED EMBODIMENTS

Figure 1:
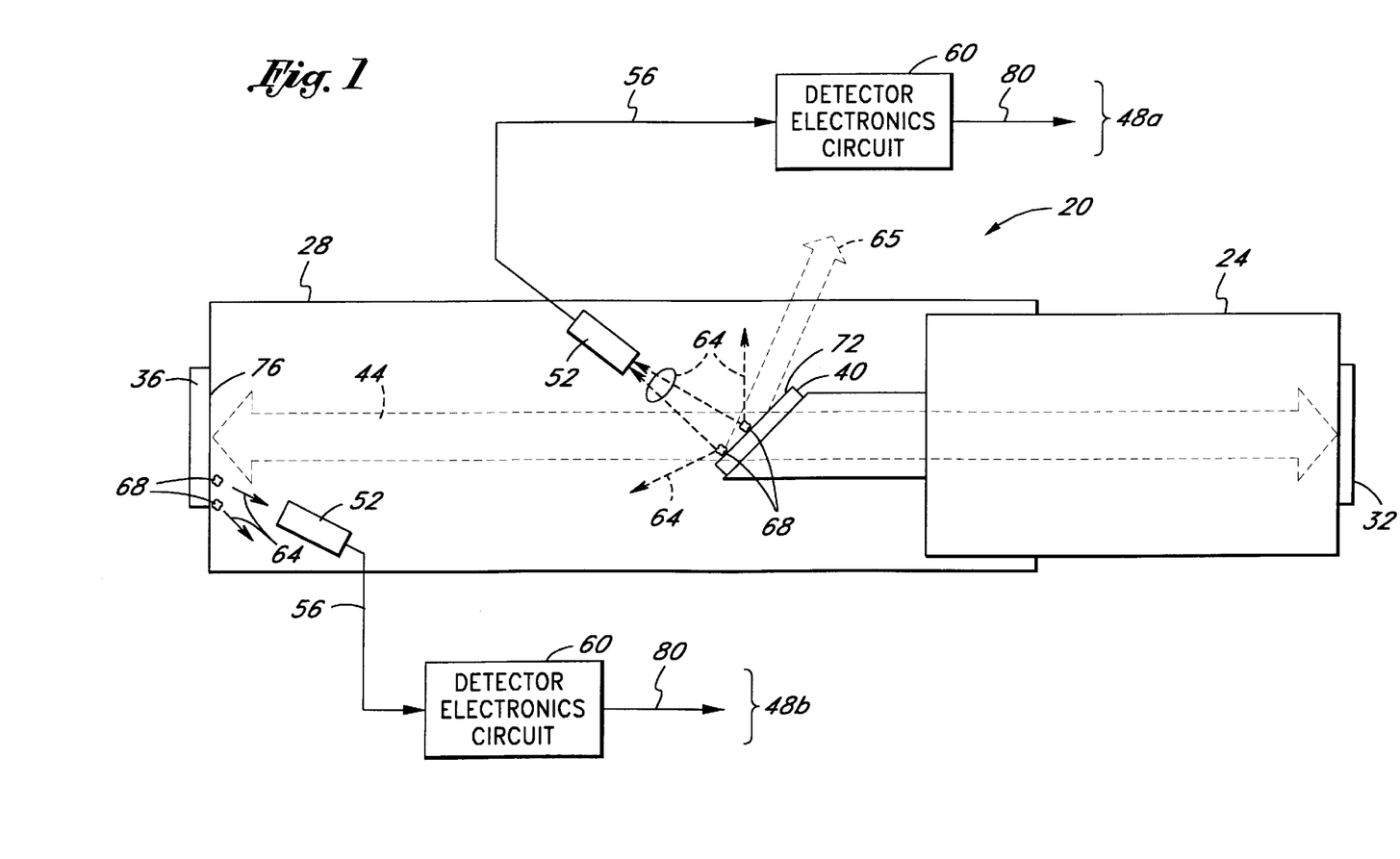
FIG. 1 illustrates a system for detecting nonspecular optical reflections from the surface of optical elements located within an optical resonant cavity which embodies various features of the present invention.

The present invention provides a photodetector for detecting diffuse scattered light, i.e., nonspecular reflections, from contamination residing on a surface of an optical element located in an optical system, thereby monitoring the performance of the optical system. As illustrated in FIG. 1, diffuse scattered light, i.e., nonspecular reflections 64, generally refers to optical energy scattered over a wide range of angles off surface irregularities 68 on an otherwise smooth reflective surface 72 of an optical element. Specular reflection 65, to be distinguished from diffuse scattered light/nonspecular reflection 64, refers to optical energy generally reflecting at a specific angle off of a clean, smooth surface 72 of an optical element, where such angle is related to the angle of incidence between the incident optical energy 44 and the surface 72.

PART ONE

Referring now to FIG. 1, there is shown an optical resonant cavity 20 which includes a plasma discharge tube 24 positioned at one end of a plasma tube housing 28. A first reflector 32 mounted at one end of the plasma discharge tube 24 and a second reflector 36 optically aligned with the first reflector 32 and mounted at the end of the plasma tube housing 28 opposite the reflector 32 together define the length of the optical resonant cavity 20. A Brewster window 40 may preferably be mounted at the end of the plasma discharge tube 24 opposite the first reflector 32 so as to be interposed between the first and second reflectors 32 and 36, respectively. A lasing gas mixture, not shown, capable of lasing is confined within the plasma discharge tube 24. Optical energy in the form of an optical beam 44 is output by the plasma discharge tube 24 through the Brewster window 40 and resonates between the reflectors 32 and 36. The Brewster window 40 may be employed for low-loss transmission of a particular polarization state of optical beam 44. The reflectors 32 and 36, and Brewster window 40 each may be categorized as an optical element, i.e., a structure that, for example, reflects, refracts, filters, and/or changes the polarization state of an optical beam.

As shown in FIG. 1, the optical resonant cavity 20 may include one or more photodetector circuits 48a and 48b for detecting nonspecular optical signals 64 reflecting off of the optical elements within the optical resonant cavity 20. Hereinafter, the photodetector circuits 48a and 48b may be referenced collectively as photodetector circuits 48. Photodetector circuits 48 each include a photodetector 52 which generates an output signal 56 which is provided to a detector electronics circuit 60 for suitable signal processing. The output signal 56 represents the intensity of nonspecular optical signals 64 scattered from particulate contamination 68 on the various optical elements in the optical resonant cavity 20. By way of example: 1) photodetector 52 of photodetector system 48a preferably is positioned within the plasma tube housing 28 so as to detect the intensity of nonspecular optical signals 64 scattering from any particulate contamination 68 accumulated on the surface 72 of the Brewster window 40; and 2) photodetector 52 of photodetector system 48b is positioned within the plasm tube housing 28 so as to detect the intensity of nonspecular optical signals 64 scattering from any particulate contamination 68 accumulated on the surface 76 of reflector 36.

For purposes of illustration, the operation of photodetector system 48a, described below, is equally applicable to the operation of photodetector system 48b. An output signal 56 generated by photodetector 52 is preferably provided to a detector electronics circuit 60 for suitable signal processing. Detector electronics circuit 60 generates an output signal 80 representing the intensity of nonspecular optical signals 64 detected by the photodetector 52. The output signal 80 may be provided to a data processor (not shown) or to a display (not shown). By way of example, the photodetector 52 may be a photodiode, photomultiplier (PM) tube, phototransistor, or any other device capable of detecting optical energy. Increases in the intensity of nonspecular optical signals 64 correspond to increased particulate contamination 68 on the surface 72 of the Brewster window 40. By way of example, an increase in the intensity of nonspecular optical signals 64 causes an increase in the level of output signal 56 generated by photodetector 52; and a decrease in the intensity of nonspecular optical signals 64 causes a decrease in the level of output signal 56 generated by photodetector 52.

The example of optical resonant cavity 20 illustrated in FIG. 1 shows two photodetectors 52 positioned to detect nonspecular reflections from the Brewster window 40 and reflector 36. However, it is to be understood that the scope of the invention includes positioning any number of photodetectors within the optical resonant cavity 20 so as to detect nonspecular reflections from any number of optical elements that may be included within the optical resonant cavity.

Figure 2:
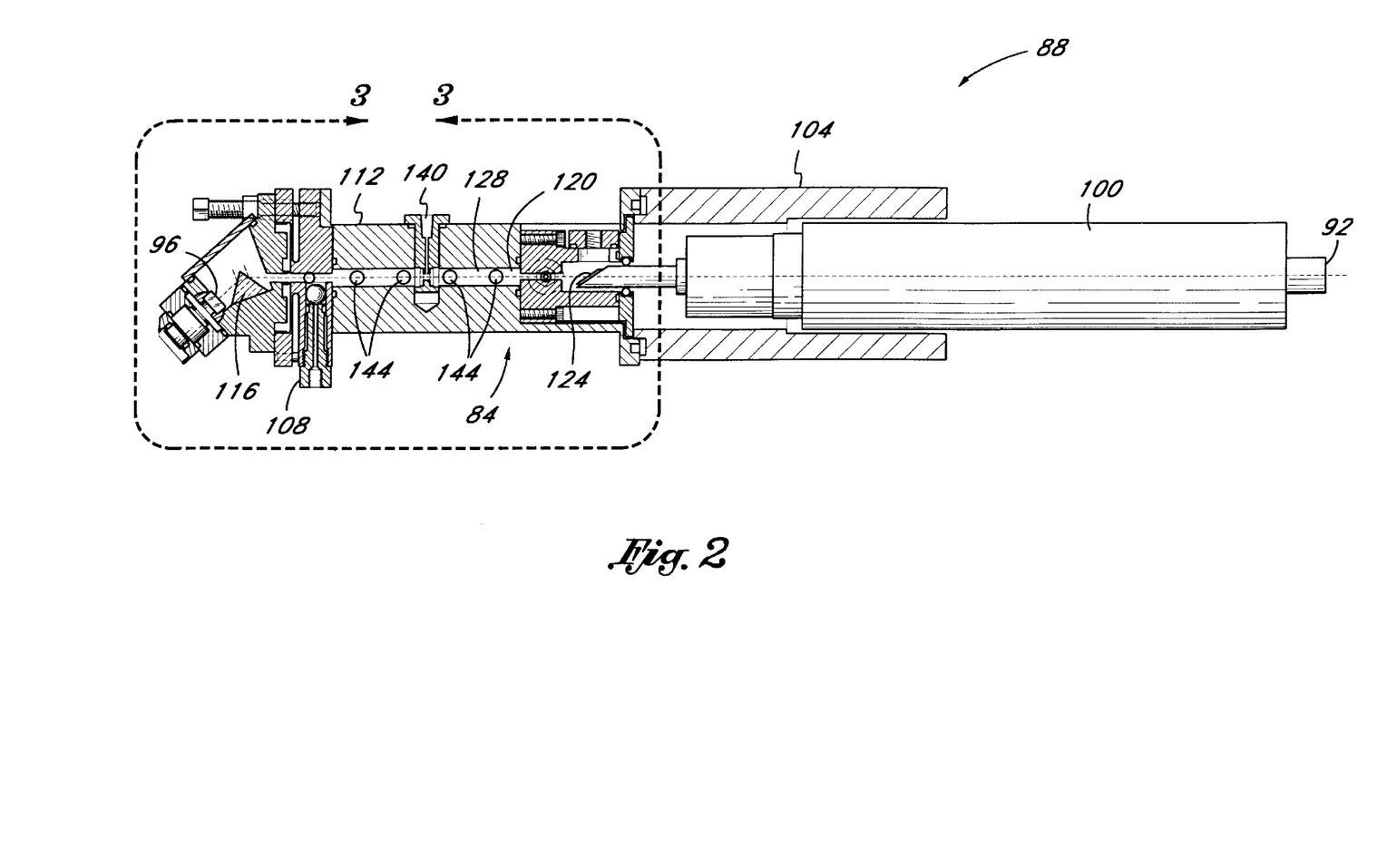
FIG. 2 illustrates an example of a particular embodiment of a system for detecting nonspecular optical reflections from the surfaces of optical elements located within a Raman gas analysis system.
Figure 3:
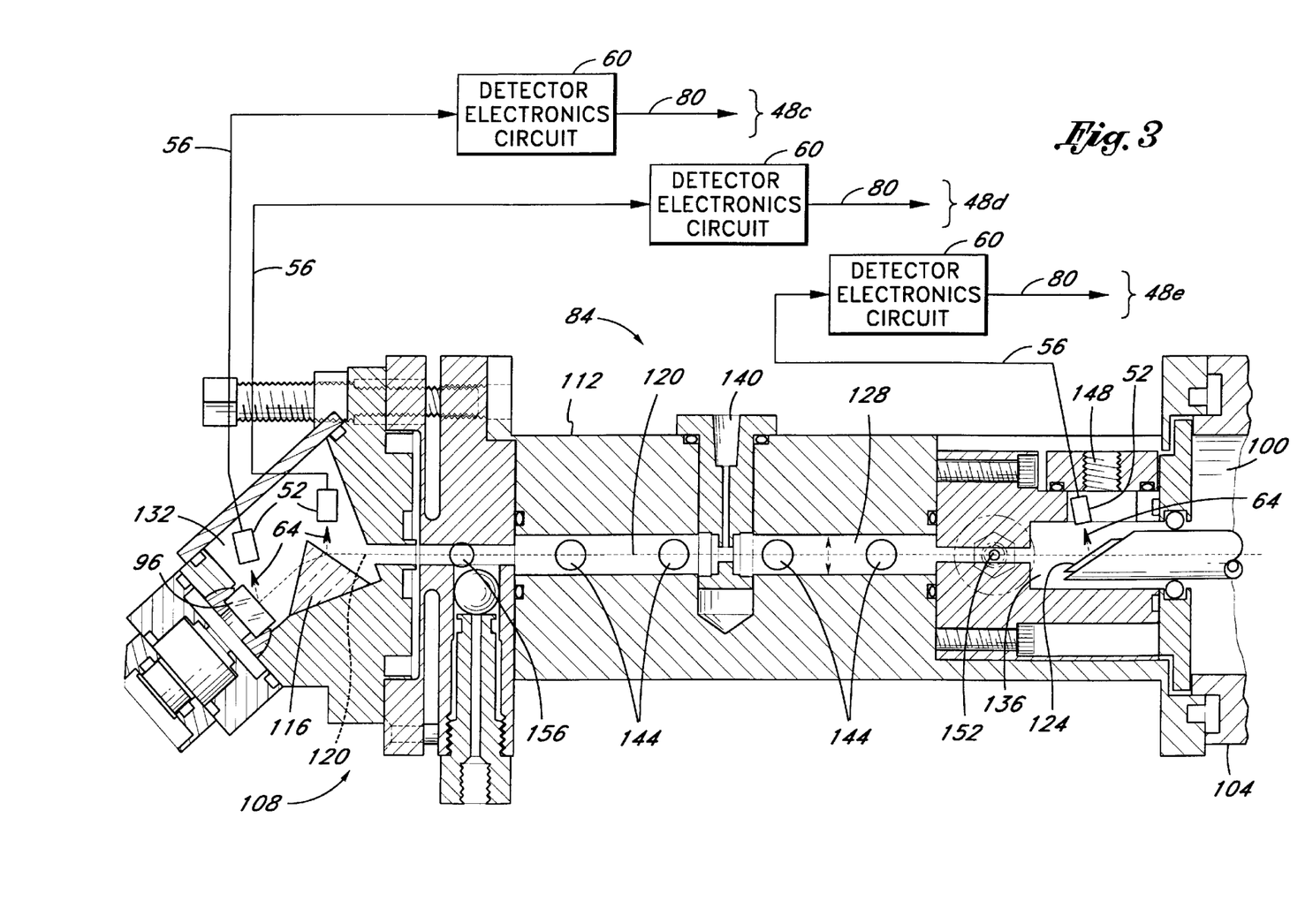
FIG. 3 is an enlarged view of a section of the Raman gas analysis system illustrated in FIG. 2.

Referring to FIG. 2, a second embodiment of the present invention provides a photodetector circuit for monitoring the level of nonspecular reflection from the optical elements in a gas analysis cell 84 in a Raman gas analysis system 88 in order to determine the level of particulate contamination at various locations within the system. The Raman gas analysis system 88 illustrated in FIGS. 2 and 3 is thoroughly described in U.S. patent application Ser. No. 08/366,840, entitled "RAMAN GAS ANALYSIS SYSTEM WITH PRECISION OPTICAL ALIGNMENT FEATURES", incorporated in its entirety herein by reference. This system has an optical resonant cavity which includes a plasma discharge tube 100 and has a volume which is defined by a first reflector 92 and a second reflector 96. The plasma discharge tube 100 is affixed within one end of a plasma tube housing 104. The second reflector 96 is supported by an optical alignment structure 108 mounted to the end of a housing 112 opposite the plasma discharge tube 100. The first reflector 92 is preferably a high reflectivity mirror having a reflectivity greater than 99.9%. The second reflector 96 preferably comprises a second high reflectivity mirror. A Brewster prism 116 is preferably inserted in the cavity to select a particular wavelength and polarization state of light beam 120. The light beam 120 resonates along a path in the gas analysis system 88 between the first and second reflectors 92 and 96. Such path defines an optical resonant cavity. A lasing gas mixture capable of lasing is confined within the plasma discharge tube 100 and a Brewster window 124 is positioned at the end of the discharge tube 100 adjacent the output such that the light beam 120 resonating within the optical resonant cavity enters and exits the discharge tube 100 through the Brewster window 124.

As shown in FIGS. 2 and 3, the gas analysis cell 84 is positioned intermediate the Brewster window 124 and second reflector 96 within the optical resonant cavity. The analysis cell 84 comprises housing 112 which encloses an analysis chamber 128. The housing 112 is mounted to an end of the plasma tube housing 104 opposite the plasma discharge tube 100. The analysis cell 84 includes two buffer gas regions 132 and 136 on either end of the analysis chamber 128. The analysis chamber 128 is connected to a source of sample gas to be analyzed by a gas sample inlet port 140. The gas analysis cell 84 further comprises a plurality of output channels 144 which have optical axes approximately perpendicular to the optical axis of the laser resonator and which form optical passageways between the analysis chamber 128 and the outside of the gas cell 84. A first buffer gas inlet port 148 is connected to the buffer region 136 adjacent the Brewster window 124 and a second buffer gas inlet port (not shown) is connected to the buffer region 132 adjacent the Brewster prism 116 and second reflector 96. Additionally, the gas cell 84 includes a first output port 152 connected to the buffer region 136 at the end of the analysis chamber 128 nearest the Brewster window 124. The output port 152 is positioned intermediate the gas sample inlet port 140 and the first buffer gas inlet port 148. A second output port 156 is connected to the buffer region 132 at the end of the analysis chamber 128 nearest the second reflector 96. The output port 156 is positioned intermediate the gas sample inlet port 140 and the second buffer gas inlet port.

Referring to FIG. 3, the Raman gas analysis system 88 may include one or more photodetector circuits, as for example, photodetector circuits 48c, 48d, 48e, collectively referenced as photodetector circuits 48. Photodetector circuits 48 each include a photodetector 52 which generates an output signal representing the intensity of nonspecular optical signals 64 reflecting off the various optical elements in the Raman gas analysis system 88 that are detected by the photodetector circuits 48. By way of example: 1) photodetector 52 of photodetector system 48c preferably is positioned within the buffer gas region 132 to detect the intensity of nonspecular optical signals 64 reflecting off the surface of second reflector 96; 2) photodetector 52 of photodetector system 48d is positioned within buffer gas region 132 to detect the intensity of nonspecular optical signals 64 reflecting off the surface of the prism 116; and 3) photodetector 52 of photodetector system 48e is positioned within buffer gas region 136 to detect the intensity of nonspecular optical signals 64 reflecting off the surface of the Brewster window 124.

It is to be understood that the operation of photodetector system 48e, described below, is equally applicable to the operations of photodetector systems 48c and 48d. Still referring to FIG. 3, photodetector circuit 48e includes a photodetector 52 mounted within the buffer gas region 136 so as to detect nonspecular optical signals 64, if present, reflecting off any particles or residue (not shown) residing on the surface of Brewster window 124. An output signal 56 of photodetector 52 is provided to a detector electronics circuit 60 for signal processing. Detector electronics circuit 60 generates an output signal 80 representing the intensity of nonspecular signals 64 detected by the photodetector 52. The output signal 80 may be provided to a data processor (not shown) or to a display (not shown) to indicate the intensity of nonspecular signals 64 detected by the photodetector 52. The photodetector 52 may be a photodiode, photomultiplier (PM) tube, phototransistor, or any other device capable of detecting optical energy. Increases in the intensity of nonspecular signals 64 correspond to increased particulate contamination on the surface of the Brewster window 124. By way of example, an increase in the intensity of nonspecular optical signals 64 causes an increase in the level of output signal 56 generated by photodetector 52; and a decrease in the intensity of nonspecular optical signals 64 causes a decrease in the level of output signal 56 generated by photodetector 52.

FIG. 3 shows three photodetector systems 48 employed to detect nonspectral optical signals 64 reflecting off the various optical elements in the optical resonant cavity. However, it is to be understood that the scope of the invention includes the use of any number of photodetector systems to detect nonspectral optical signals reflecting off one or more of the optical elements in the optical resonant cavity.

With reference to FIG. 3, a gas sample which is to be analyzed enters the sampling cell 84 through the inlet port 140 and is contained within the analysis chamber 128. The laser discharge tube 100 emits a light beam 120 having characteristic wavelengths dependent upon the type of lasing gas within the discharge tube 100. The wavelength(s) and polarization of the light beam 120 resonating within the cavity are selected by the orientation of the Brewster prism 116, and the nature of the mirrored coatings on the reflecting end mirrors 92 (FIG. 2) and 96. The light beam 120 resonates over a distance between the first and second reflectors 92 and 96 through the length of the analysis chamber 128 of the gas analysis cell 84 and through Brewster prism 116. Such distance defines the length of the optical resonant cavity. Brewster window 124 seals the gas within the discharge tube 100 while also providing polarization control of the light beam 120 by completely transmitting light having a preferred polarization state.

Inside the analysis chamber 128 of the sample cell 84, the light beam 120 resonating in the optical resonant cavity passes through the sample of the gas to be analyzed. The Raman scattered radiation from the gas sample is collected over as large a solid angle as possible by individual detector channels 144, which are located approximately perpendicular to and on either side of the axis of the light beam 120. The Raman signals can then be collected by optics, sensed by detectors and analyzed with a microprocessor (not shown) associated with the detector channels 144. Based on such analysis, the identity and concentration of each specific gas comprising the gas sample contained within the analysis chamber 128 can be determined. A more detailed description of this analysis process can be found in U.S. Pat. No. 4,784,486, entitled "MULTI-CHANNEL MOLECULAR GAS ANALYSIS BY LASER-ACTIVATED RAMAN LIGHT SCATTERING", issued to Van Wagenen et al., assigned to the assignee of the present application and incorporated herein by reference. Further detailed descriptions of various aspects of Raman Gas Analysis systems are disclosed in commonly assigned U.S. Pat. No. 5,135,304, entitled "GAS ANALYSIS SYSTEM HAVING BUFFER GAS INPUTS TO PROTECT ASSOCIATED OPTICAL ELEMENTS", issued to Miles et al.; U.S. Pat. No. 5,153,671, entitled "GAS ANALYSIS SYSTEM HAVING BUFFER GAS INPUTS TO PROTECT ASSOCIATED OPTICAL ELEMENTS", issued to Miles; U.S. Pat. No. 5,245,405, entitled "CONSTANT PRESSURE GAS CELL", issued to Mitchell et al., and U.S. patent application Ser. No. 08/366,840, entitled "RAMAN GAS ANALYSIS SYSTEM WITH PRECISION OPTICAL ALIGNMENT FEATURES", each of which is hereby incorporated herein by reference.

PART TWO

Figure 4:
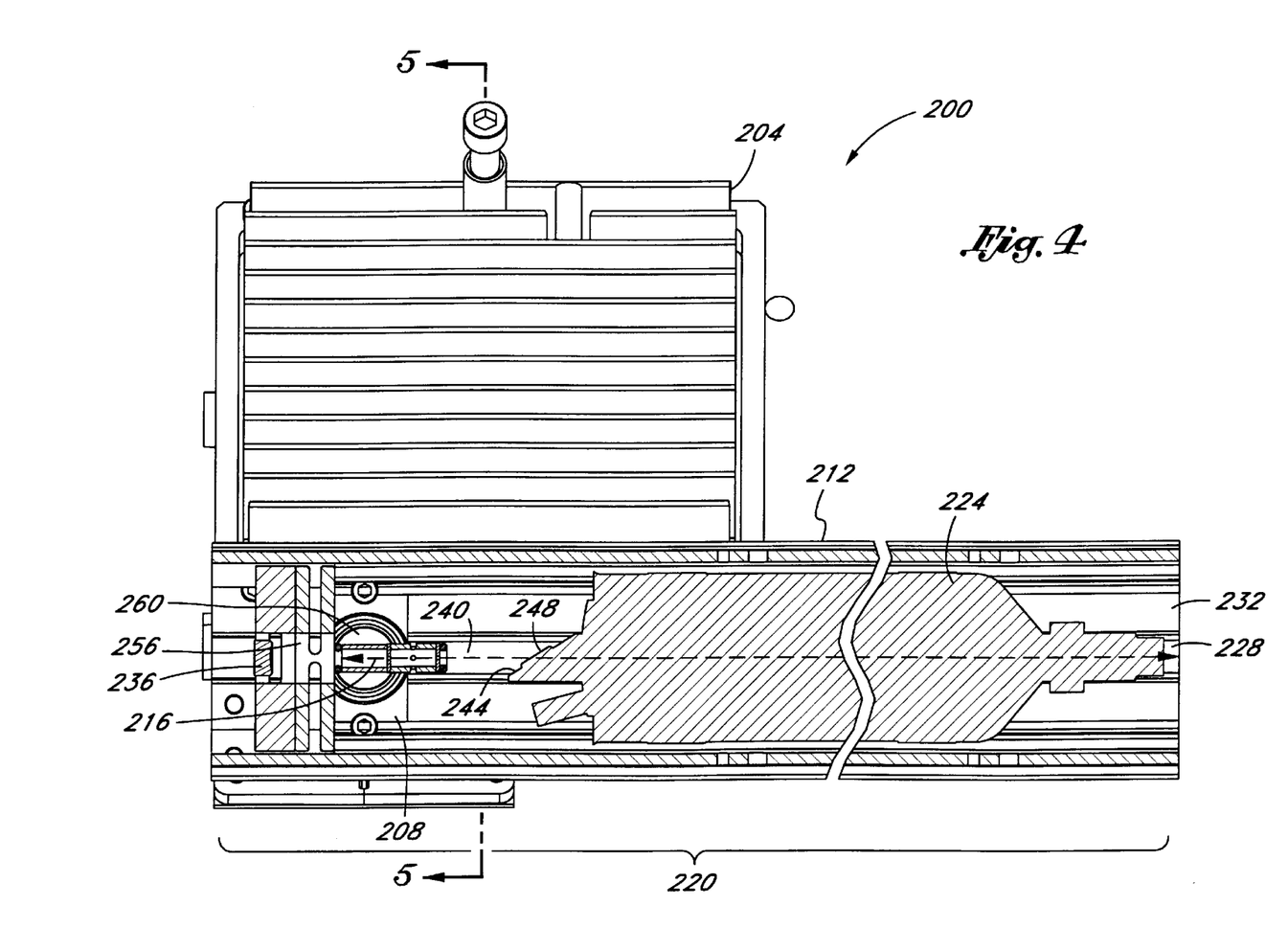
FIG. 4 is a cross-sectional view of a Raman spectroscopy system embodying various features of the present invention.

Referring to FIG. 4, there is shown a cross-sectional view of a Raman spectroscopy system 200 embodying various features of the present invention. A Raman spectroscopy system is used to analyze the constituents of a gas based upon the spectral components of optical energy resulting from interaction between the optical energy and the gas. Raman spectroscopy system 200 includes a detector unit 204, a gas sample cell subsystem 208, and a plasma tube housing 212. The gas sample cell subsystem 208 includes sample gas inlet and outlet ports (not shown) by which sample gas may be admitted and exhausted from a transparent gas sample cell 216 mounted in the gas sample cell subsystem 208.

Figure 5:
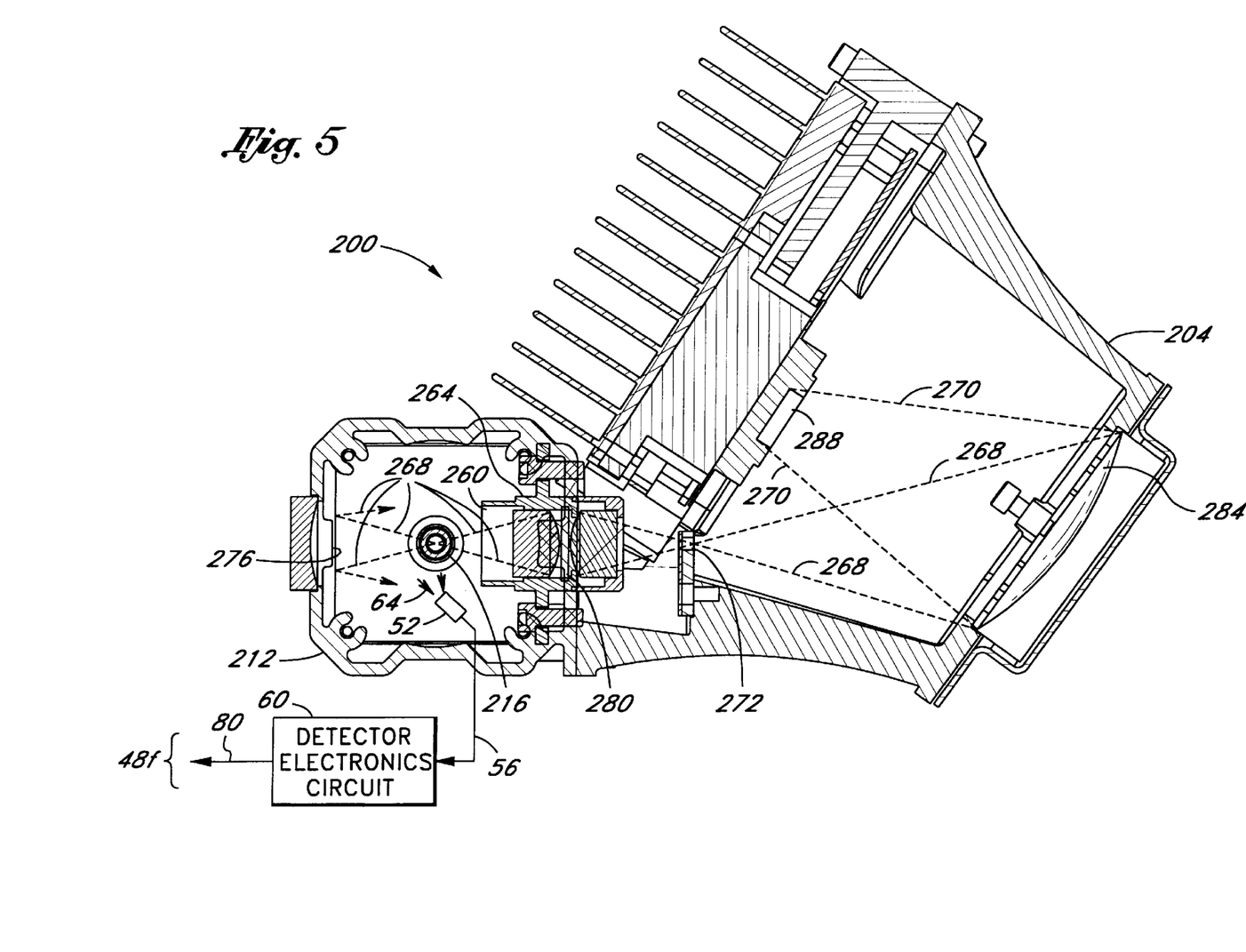
FIG. 5 is a cross-sectional view of the Raman spectroscopy system of FIG. 4 taken along line 5—5.

FIG. 5 is a cross-sectional view of the Raman spectroscopy system 200 taken along line 5—5 of FIG. 4. Referring to FIGS. 4 and 5, the gas sample cell subsystem 208 is positioned within a laser resonant cavity 220 comprising an optical gain system, such as a plasma discharge tube 224, a first mirror 228 mounted at a first end 232 of the plasma discharge tube 224 and a second mirror 236 optically aligned with the first mirror 228.

The plasma discharge tube 224 generates and emits a light beam 240 which resonates within the resonant cavity 220 between the mirrors 228 and 236, thereby defining a laser. By way of example, the plasma discharge tube 224 may preferably be implemented as a Helium-Neon plasma discharge tube sealed by the first mirror 228 at end 232 and by a Brewster window 248 at end 244. The first mirror 228 is integrally mounted to the plasma discharge tube 224 in a pre-aligned, sealed configuration. The Brewster window 248 selects a single polarization state for the light beam 240. Plasma discharge tubes suitable for use in the present invention may be of the type commercially available from Melles Griot Laser Division in San Diego, Calif., such as Model No. 05-LHB-566. While the description of the plasma discharge tube 224 is described above as a Helium-Neon plasma discharge tube, it is to be understood that the optical gain system alternatively may be implemented using other types of lasers, e.g., other gas lasers, solid state lasers or laser diodes.

As illustrated in FIG. 4, the plasma tube housing 212 may be mounted to the gas sample cell subsystem 208 using a gas-tight, interference fit which preferably may be of the type described in co-pending U.S. patent application Ser. No. 08/366,840, filed Dec. 30, 1994, entitled "Raman Gas Analysis System with Precision Optical Alignment Features," incorporated herein by reference, and assigned to the assignee of the present application. The second mirror 236 preferably is mounted on a precision optical positioning system 256 mounted to the end of the gas sample cell 208, as for example, by threaded screws, not shown. The precision optical positioning system 256 preferably may be of the type described in co-pending U.S. patent application Ser. No. 08/366,840, filed Dec. 30, 1994, entitled "Raman Gas Analysis System with Precision Optical Alignment Features", referenced herein above. The precision optical alignment system 256 is adjustable to provide extremely precise angular adjustments of the position of the second mirror 236 to optimize resonance of the light beam 240 within the resonant cavity 220.

The reflectivity of the second mirror 236 of the laser resonant cavity 220 may be such that light loss from the system 200 is in the range of about 1000 parts per million (ppm) to 2500 ppm. This loss level provides light beam 240 sufficient power to provide an adequate Raman signal, while obviating the need to place a prism in front of the second mirror 236 so that the light beam 240 incident on the mirror 236 has a single lasing wavelength.

As shown in FIGS. 4 and 5, the gas sample cell subsystem 208 is provided with a light output port 260. Collection optics 264 are optically coupled to the light output port 260. The collection optics 264 gather light signals 268 emitted from the gas cell 216 that are directed to the light output port 260. Collection optics 264 direct the light signals 268 to an entrance slit 272 of the detector unit 204. Preferably, the slit 272 is rectangularly shaped having a longitudinal axis which is parallel to the light beam 240. Mirror 276 mounted to the side of plasma tube housing 212 reflects any incident light signals 268 towards the collection optics 264 to increase the signal strength of the light signals 268 which are focused on the entrance slit 272. A laser line rejection filter 280 preferably is included in the optical path between the light output port 260 and the entrance slit 272 to filter out scattered light having the wavelength of the light beam 240 circulating within the laser resonant cavity 220.

The detector unit 204 further includes a reflecting holographic grating 284 and an array detector 288. In one embodiment of the system 200, the holographic grating 284 may be approximately 50 mm in diameter, and have a focal length of approximately 100 mm and a groove density of 1110 grooves/mm. Such a grating may be purchased from American Holographic, in Littleton, Mass. as Part No. 491.75.

Raman scattered light signals 268 scattered by a gas sample contained in the gas sample cell 216 pass through the light output port 260 and are collected, filtered, and focused on the entrance slit 272 by the collection optics 264 and laser line rejection filter 280. Typically, the Raman scattered light signals 268 comprise a plurality of discrete wavelengths. After passing through the entrance slit 272, the Raman scattered light signals 268 are incident on the reflecting holographic grating 284. The reflecting holographic grating 284 separates the plurality of discrete wavelengths comprising light signals 268 into discrete wavelength light signals 270. The discrete wavelength light signals 270 are reflected and focused by the reflecting holographic grating 284 onto the array detector 288. By way of example, array detector 288 may preferably be implemented as a charge-coupled device (CCD) array detector. The reflecting holographic grating 284 preferably projects a rectangular or square image of the entrance slit 272 onto the array detector 288.

CCD detector 288 advantageously converts light signals 270 into signals which are indicative of the intensities of the discrete wavelength light signals 270 comprising light signals 268. The CCD detector 288 may be implemented as an 512×128 pixel device. Such a CCD detector may be purchased from Hamamatsu Photonics KK, Hamamatsu City, Japan, as a single, hermetically-sealed package which includes a TE cooler as part number S5769-0907.

As shown in FIG. 5, the plasma tube housing 212 may include a photodetector circuit 48f for detecting nonspecular optical signals scattered from particulate contaminates on the optical elements within the plasma tube housing 212. Hereinafter, the photodetector circuit 48f may also be referenced as photodetector circuit 48.

Photodetector circuit 48f is generally identical in operation to photodetector circuits 48a–48e, described herein above. By way of example, photodetector 52 of photodetector system 48f preferably is positioned within the plasma tube housing 212 so as to detect the intensity of nonspecular optical signals 64 scattered from any particulate contamination accumulated on the surface of any optical component of the gas sample cell 216, the mirror 236 or the Brewster window 248.

PART THREE

Figure 6:
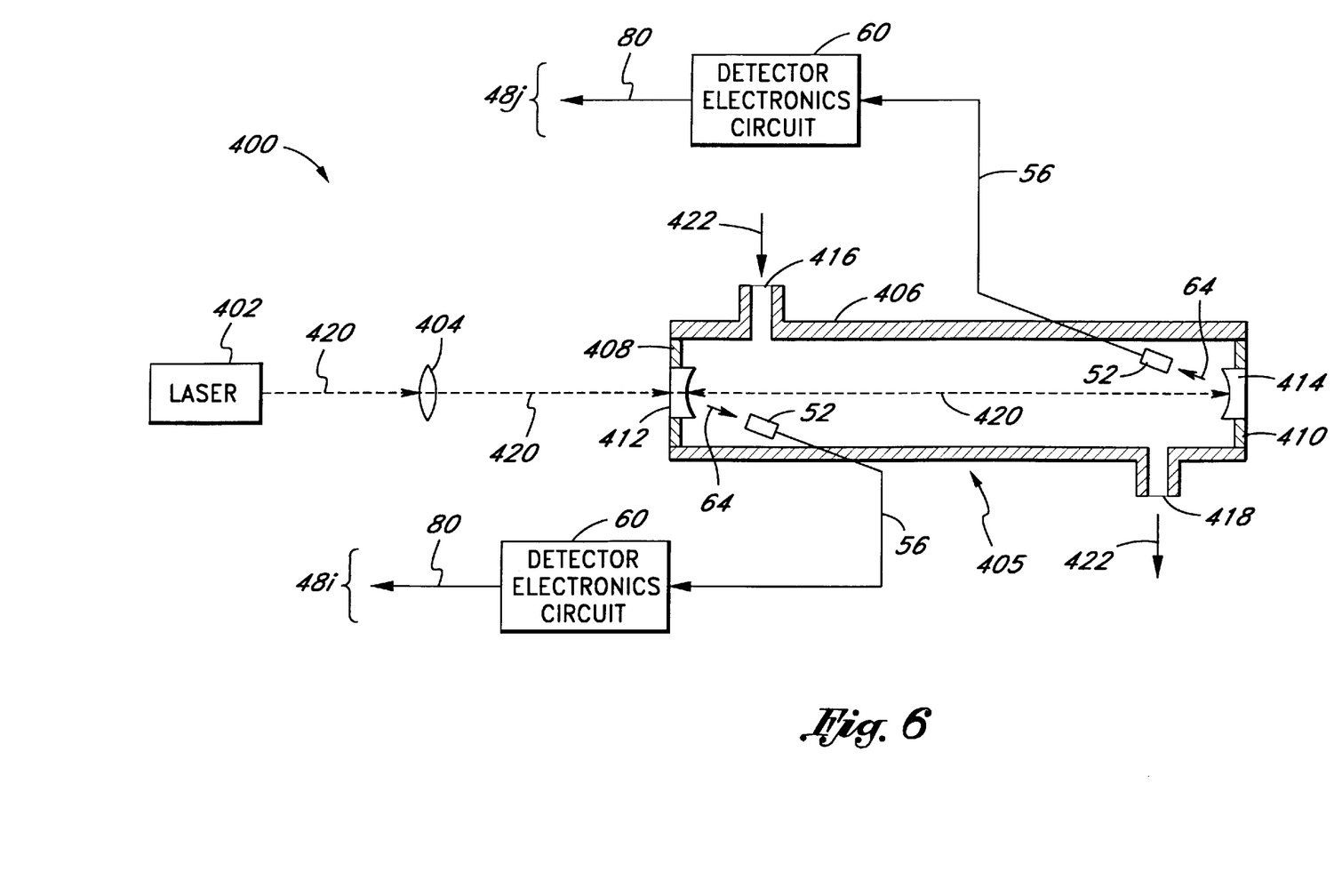
FIG. 6 shows another Raman spectroscopy system embodying various features of the present invention.

Referring to FIG. 6, there is shown a Raman gas analysis system 400 embodying various features of the present invention and having a passive optical resonant cavity which includes photodetector circuits for monitoring the level of any nonspecular reflections off any particulate contamination accumulated on the optical elements within the cavity. A passive optical resonant does not include an optical power source within the cavity, i.e., optical power is supplied by a source external to the cavity.

The Raman gas analysis system 400 includes a laser 402, an optics system 404, and a gas analysis cell 405. The gas analysis cell 405 comprises a tube 406 having opposed gas tight end seals 408 and 410. A partially reflective mirror 412 is mounted to end seal 408 and a reflective mirror 414 is mounted to end seal 410. By way of example, the mirrors 412 and 414 are preferably concave mirrors having reflective surfaces which face each other and have coincident optical axes to define an optical resonant cavity therebetween. Gas inlet port 416 and gas outlet port 418 allow gas to be introduced and exhausted from the gas analysis cell 405.

The gas analysis system 400 further includes photodetector circuits 48i and 48j for detecting nonspecular reflections off particles accumulated on the optical elements, i.e., mirrors 412 and 414, within the gas analysis cell 405. Photodetector circuits 48i and 48j are preferably identical in construction and operation to photodetector circuits 48a–48f, described herein above. Photodetector 52 of photodetector circuit 48i is mounted within the gas analysis cell 405 so as to detect nonspecular optical signals 64 reflecting off any particulate contamination accumulated on mirror 412. Likewise, photodetector 52 of photodetector circuit 48j is mounted within the gas analysis cell 405 so as to detect nonspecular optical signals 64 reflecting off any particulate contamination accumulated on mirror 414.

In the operation of Raman gas analysis system 400, laser 402 generates a laser beam 420 which is directed by optics system 404 through partially reflective mirror 412 into the gas analysis cell 405. After being injected into the gas analysis cell 405, the laser beam 420 is reflected by mirror 414 back to mirror 412, and thereby resonates therebetween. The laser beam 420 may be Raman shifted as a result of the interaction between the gas 422 which passes through the gas analysis cell 405. Particulate contamination (not shown) accumulated on the surfaces of mirrors 412 and 414 results in nonspecular optical signals 64 reflecting off the mirrors. The optical signals 64 are detected by corresponding photodiodes 52 of photodetector circuits 48i and 48j. Thus, the present invention provides a system for monitoring the level of particulate contamination on the optical elements within the gas analysis cell.

It is to be understood that the present invention provides a method and system for monitoring the level of particulate contamination within an optical system by detecting nonspecular optical radiation reflected from the surfaces of optical elements within the system. In light of these teachings, numerous other embodiments of the invention may become obvious to one skilled in the art. For example, while the invention has been described in terms of monitoring contamination on optical elements in a resonant and also a non-resonant cavity, and more particularly, in a Raman gas analysis system, it is to be understood that the invention also applies to any optical system wherein monitoring contamination on optical elements is desirable. Thus, the system and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A system for detecting contamination on a surface of an optical element in an optical system comprising:
   a laser having a resonant cavity, wherein said laser is disposed to generate a beam of optical radiation for transmission in the optical system and irradiation of the optical element, wherein the optical element is located within said laser resonant cavity;
   a contamination detector positioned to detect nonspecular optical energy scattered from the surface of the optical element;
   a contamination detector circuit operably coupled to said contamination detector to receive signals from said contamination detector which are representative of an intensity of the nonspecular optical energy scattered from the surface of the optical element detected by said contamination detector, said contamination detector circuit having an output which produces an electronic signal which is representative of the intensity of the nonspecular optical energy scattered from the surface of the optical element;
   a gas sample cell configured to receive and hold a gas sample in an interior region of said gas sample cell, wherein said gas sample cell is positioned in said laser resonant cavity such that said beam of optical radiation from said laser passes through said gas sample; and
   a scattered light detector positioned with respect to said gas sample cell such that it receives and detects light scattered out of said laser beam by the gas sample.

2. The system of claim 1 wherein said contamination detector further comprises one of either a photodiode, a photomultiplier tube or a phototransistor.

3. The system of claim 1 wherein said contamination detector is mounted within said laser resonant cavity.

4. A method for detecting contamination of an optical element in a gas analysis system comprising the steps of:
   generating a beam of laser light with a laser having a resonant cavity;
   positioning the optical element in the laser resonant cavity;
   irradiating the optical element with the beam of laser light;
   positioning an optical contamination detector with respect to the optical element such that the optical contamination detector receives nonspecular optical radiation scattered from the beam of laser light by contamination located on a surface of the optical element;
   detecting the nonspecular optical radiation scattered from the surface of the optical element;
   generating an output signal which is representative of an intensity of the nonspecular optical radiation scattered from the surface of the optical element;
   positioning a gas sample cell which contains a gas sample in an interior region of said gas sample cell in said laser resonant cavity such that said beam of laser light from said laser passes through the gas sample; and
   receiving and detecting light scattered out of said laser beam by the gas sample with a scattered light detector.

5. The method of claim 4 wherein the step of detecting the nonspecular optical radiation further comprises the step of selecting either one of a photodiode; a phototransistor or a photomultiplier tube.

6. The method of claim 4 wherein
   the step of positioning an optical contamination detector further comprises the step of positioning the optical contamination detector within the laser resonant cavity.

7. A system for detecting contamination on a surface of an optical element in a gas analysis system comprising:
   a laser having a resonant cavity, wherein said laser is disposed to generate a beam of laser light for transmission in the gas analysis system and irradiation of the optical element;
   a contamination detector positioned with respect to said optical element such that it receives and detects nonspecular light scattered from the surface of the optical element;
   a detector circuit operably coupled to said contamination detector to receive signals from said contamination detector which are representative of an intensity of the nonspecular light scattered from the surface of the optical element, said detector circuit having an output which produces an electronic signal which is representative of the intensity of the nonspecular light scattered from the surface of the optical element;
   a gas sample cell configured to receive and hold a gas sample in an interior region of said gas sample cell, wherein said gas sample cell is positioned in said laser resonant cavity such that said beam of laser light from said laser passes through the gas sample; and
   a scattered light detector positioned with respect to said gas sample cell such that it receives and detects light scattered out of said laser beam by the gas sample.

8. The system of claim 7 wherein said contamination detector further comprises one of either a ptotodiode, a photomultiplier tube or a phototransistor.

9. The system of claim 7 wherein the optical element is located within said laser resonant cavity.

10. The system of claim 7 wherein said contamination detector is mounted within said laser resonant cavity.

11. A method for detecting contamination of an optical element in a gas analysis system comprising the steps of:
   generating a beam of laser light with a laser having a resonant cavity;
   positioning the optical element in the laser resonant cavity;
   irradiating the optical element with the beam of laser light;
   positioning a contamination detector with respect to the optical element such that the contamination detector receives nonspecular reflections of optical radiation scattered from the beam of laser light by contamination located on a surface of the optical element;
   detecting the nonspecular reflections of optical radiation scattered from the surface of the optical element;
   generating an output signal which is representative of an intensity of the nonspecular reflections of optical radiation scattered from the surface of the optical element;

positioning a gas sample cell which is configured to receive and hold a gas sample in an interior region of the gas sample cell in the laser resonant cavity such that the beam of laser light from the laser passes through the gas sample; and receiving and detecting light scattered out of the laser beam by the gas sample.

12. The method of claim 11 wherein the step of detecting the nonspecular reflections further comprises the step of selecting either one of a photodiode; a phototransistor or a photomultiplier tube.

13. The method of claim 11 wherein the step of positioning a contamination detector further comprises the step of positioning the contamination detector within the laser resonant cavity.

* * * * *